United States Patent [19]

Giesy et al.

[11] Patent Number: 5,334,185
[45] Date of Patent: Aug. 2, 1994

[54] END-TO-END INSTRUMENT PLACEMENT APPARATUS

[75] Inventors: Jerry D. Giesy; Matthew W. Hoskins, both of Portland, Oreg.

[73] Assignee: Giesy Consultants, Inc., Portland, Oreg.

[21] Appl. No.: 132,118

[22] Filed: Oct. 5, 1993

Related U.S. Application Data

[63] Continuation of Ser. No. 957,509, Oct. 5, 1992, abandoned, which is a continuation-in-part of Ser. No. 722,886, Jun. 28, 1991, Pat. No. 5,152,749.

[51] Int. Cl.$^5$ .................... A61M 5/178; A61M 25/00
[52] U.S. Cl. ...................................... 604/164; 604/283
[58] Field of Search ............... 604/164, 166, 171, 103, 604/264, 280, 283

[56] References Cited

U.S. PATENT DOCUMENTS

| | | | |
|---|---|---|---|
| 4,326,516 | 4/1982 | Schultz et al. | 604/283 |
| 4,431,426 | 2/1984 | Groshong et al. | 604/164 |
| 4,758,219 | 7/1988 | Sacks et al. | 604/164 |
| 4,763,667 | 8/1988 | Manzo | 604/164 |
| 4,824,435 | 4/1989 | Giesy et al. | 604/49 |
| 4,969,879 | 11/1990 | Lichte | 604/283 |
| 5,074,848 | 12/1991 | Clegg et al. | 604/164 |
| 5,116,309 | 5/1992 | Coll | 604/164 |
| 5,152,749 | 10/1992 | Giesy et al. | 604/164 |
| 5,163,911 | 11/1992 | Sirimanne et al. | 604/164 |

OTHER PUBLICATIONS

Lubri-Flex TM Hydrophilic-Coated Stent.
Speed Lok TM Ureteral Stent Set.
Kwart Retro-Inject TM Stent Sets.

Primary Examiner—John G. Weiss
Attorney, Agent, or Firm—Keith A. Cushing

[57] ABSTRACT

A surgical apparatus for the placement of an instrument within a body cavity which comprises a placement device including an elongate element with an exposable tissue piercing tip, a first coupling means adjacent to the tip, and means for selectively exposing the tip; and an elongate instrument for placement including a second coupling means adapted to be coupled to the first coupling means to effect an end to end coupling of said device and said instrument whereby said instrument is positioned within said body cavity. Preferably the instrument is a suprapubic instrument for placement within a bladder. A method for placement of a suprapubic instrument is also disclosed. Also shown is a method and apparatus for end-to-end instrument coupling in the context of guidewire instrument placement. End-to-end coupling is accomplished by loop and slot arrangements, a tail and collapsing loop arrangement, and a tail captured between two slidably disposed sleeves.

8 Claims, 8 Drawing Sheets

FIG. 17 ered for issuance Oct. 6, 1992 as U.S. Pat. No. 5,152,749.

END-TO-END INSTRUMENT PLACEMENT APPARATUS

RELATED APPLICATION

This is a continuation of copending application Ser. No. 07/957,509 filed on Oct. 5, 1992 now abandoned which application is a continuation-in-part of co-pending and allowed U.S. application Ser. No. 07/722,886 filed Jun. 28, 1991 by applicants herein and allowed for issuance Oct. 6, 1992 as U.S. Pat. No. 5,152,749.

BACKGROUND OF THE INVENTION

The present invention relates to a surgical apparatus for the placement of an instrument within a body cavity. More particularly, the invention relates to an apparatus, device and method for end-to-end instrument placement.

Suprapubic catheters and instruments are used in many clinical settings including cases involving female incontinence, transurethral resection of the prostate where continuous irrigation is used, neurogenic bladders, spinal cord injury and other cases where bladder drainage and/or healing are desired. Additionally suprapubic instruments are used for inspection and therapy of the bladder, prostate, and/or ureter. Suprapubic catheterization offers a number of advantages over transurethral catheterization. These advantages include increased patient comfort, minimization of infection, improved irrigation and drainage during and after resection of the prostate, easier replacement and superior convenience during long-term catheterization, and improved evaluation of voiding and residual urine when applicable. Also, the suprapubic site is a convenient access route for instruments to observe and treat various conditions, the design, shape, and size of the instrument not being restricted by the shape and size of the urethra or concerns of urethral injury.

U.S. Pat. No. 4,684,369 discloses a needle for introducing a suprapubic bladder drainage instrument through the urethra. The needle is adapted to be attached at its rear end to a catheter which follows the needle through the urethra.

Current methods of placing suprapubic catheters are the "outside-to-inside" method and the less common "inside-to-outside" method. With the outside-to-inside approach, a sharp trocar or catheter-obturator combination is used to pierce from outside the body through the lower abdomen and into the bladder to create a passageway for pushing the catheter into the bladder. By comparison, the inside-to-outside method employs a grasping tool which is passed into the bladder via the urethra and, after positioning, can be pressed through the bladder and abdominal wall near the symphysis. Then grasping the catheter, it is used to pull the catheter into the bladder where the catheter may be released and left in a suprapubic placement.

While complications are rare, difficulties have been reported with percutaneous outside-to-inside suprapubic catheterization using a trocar. For example, the catheter may be placed accidentally outside of the bladder. The standard method of using a trocar/catheter arrangement does not always provide the accuracy and control needed for correct placement of the catheter. Also, outside-to-inside catheterization presents risk of injury to the floor of the bladder or damage to the bowel. Uncertainties in trocar alignment, orientation, or insertion distance can lead to such injuries. Thus, poor alignment or variable depth can result in perforation of the peritoneum, incomplete bladder entry, or penetration of the posterior bladder wall. Furthermore, due to a limited choice of catheter sizes and types, inadequate catheter lumen size may result. Finally, inappropriate suprapubic puncture size may result in extravasation of urine around the catheter or into the retroperitoneum.

Use of the inside-to-outside technique can minimize the above problems, but the lack of well designed devices for performing the procedure has limited its adoption. With the inside-to-outside method, a curved grasping tool is passed through the urethra and its tip is pushed against the bladder dome and anterior abdominal wall. Suprapubic palpation enables the practitioner to select a desired penetration site. The curved tool is pressed against the bladder dome and in some cases forced through the bladder, fascia, and abdominal wall. In other techniques, an incision is extended from the exterior abdominal wall on to the instrument tip permitting its advancement. Once outside the abdomen, the device is coupled to the drainage tube in some fashion so that the tube is guided into the bladder. Once within the bladder, the drainage tube is released. The device is then removed by way of the urethra.

While various instruments which utilize the inside-to-outside approach exist, none have coordinated the penetration, coupling, and release functions. Currently used instruments include the Lowsley retractor, uterine packing forceps (for females), and modified urethral sound. In general, these instruments require many steps, lack uniformity, and are not always readily available. Use of such instruments often results in ineffective penetration, inadvertent loss of the catheter, and poor sealing between the catheter and bladder wall.

Improvements in the suprapubic instrument placement may be applied to other medical applications. For example, in substantially non-invasive methods of internal operations, e.g. laproscopic surgery, the practitioner accesses internal organs through small incisions and working sheaths. The instruments used in such operations are generally elongate and adapted for use by way of these small incisions or sheaths. Accordingly, improvements in placement of suprapubic instruments, which are generally elongate instruments, may be applied to such substantially noninvasive operations.

Placing in-dwelling drainage tubes such as ureteral stents can be difficult due to their lack of column strength, frictional forces, and the fact that direct control of their proximal end is typically lost once the stent entirely enters a body lumen. Various placement techniques have been employed to overcome these problems, but without providing the extent of instrument placement control a practitioner would desire. Such placement techniques include stent placement over a guidewire using a pushing tube to advance the stent; stent placement on a wire where the stent, guidewire and pusher advance as one; and stent placement alongside a wire using a guide-eye where the stent is pushed internally or externally at its distal tip. In use of guidewire instrument placement methods, it is desirable to leave the guidewire as free as possible because the guidewire constitutes the primary instrument access route.

U.S. Pat. No. 4,824,435 issued Apr. 25, 1989 to Jerry D. Giesy and Matthew W. Hoskins, inventors herein, shows a guide-eye instrument guidance system wherein elongate flexible elements are guided into place within a tortuous body passage by providing the elements with annular guides adjacent their distal ends and sliding the elements over a guidewire within the passage. Column strength to move the elements through the body passage may be provided by a tubular pusher slidably received on the guidewire. Several instruments, each including an annular guide at its distal end, may be sequentially or simultaneously guided into place over a single guidewire.

Under the technique and apparatus disclosed in U.S. Pat. No. 4,824,435 the instrument to be placed is slidably coupled at its distal end to a guidewire. Such slidable coupling may include a loop formation at the distal end of the instrument to be placed. For tubular instruments, a lateral cut or slot in the tube wall near the distal end slidably receives the guidewire. To mount the instrument, the guidewire is threaded into the open distal end of the tube and then out the wall opening provided by the lateral cut or slot. In either case, the instrument to be placed is slidably coupled at its distal end to the guidewire. If the instrument itself has sufficient column strength, the instrument may be positioned by application of force at its proximal end as its distal end slides along the access pathway provided by the guidewire. For instruments having insufficient column strength, a tubular pusher may be slidably and concentrically received upon the guidewire. The distal end of the pusher engages the slidably mounted distal end of the instrument to be placed to move the instrument to be placed along the guidewire and into position.

While the apparatus and method of the system shown in U.S. Pat. No. 4,824,435 has proven useful in many cases, it lacks certain instrument positioning control desired by many practitioners. In particular, the disclosed system is generally limited to pushing of instruments along a guidewire. The practitioner has limited additional positioning control over the instrument to be placed, e.g., the practitioner typically cannot retract the instrument along the guidewire.

Various technologies have also been developed to address access problems in placement of instruments within a body lumen. These technologies include higher-column strength stents, hydrophilic-coated stents, stents of hybrid materials, locking devices to lock the stent, guidewire and pusher as one.

No one instrument placement method and apparatus provides complete and versatile positioning control, i.e., pushing, pulling, and twisting, of the instrument to be placed especially in the context of guidewire instrument placement. Furthermore, those instrument placement methods available often limit the practitioner in use of other associated instrument placement methods. Present positioning systems suffer certain limitations.

In a trailing suture design, i.e., a Lubri-Flex (Registered Trademark of Surgitek) hydrophilic-coated stent, the suture trails the stent and provides retraction control during placement. Once positioning is complete the suture can be cut and pulled out or left in for use later in removing the stent. This provides reasonable control, but can be cumbersome and makes desirable a more simple coupling system.

The Speed Lok (TM) ureteral stent set available from Boston Scientific Corporation under the Registered Trademark Microvasive, is limited to one pass placement. The guidewire, stent, and pusher are designed specifically to be pre-coupled as a placement system, and cannot be employed in connection with a separate or pre-existing guidewire. The system does not offer a clean release between the pusher or positioner device and the instrument to be placed. Removal of instrument placement components can affect the position of the instrument placed. Accordingly, upon removal of the placement system following positioning of the instrument to be placed, the instrument placed may have been dislodged from its desired position.

The Kwart retro-inject (TM) stent sets require different pusher/inserter sizes for stents of different sizes. As understood, the Kwart retro-inject system coaxially mounts a stent inserter sleeve, release sleeve, and the stent upon a guidewire. Manipulation of the stent, i.e., positioning of the stent, is provided by the frictional inter-relationship among the coaxially mounted elements. Once the stent is positioned, one of the coaxially mounted elements is removed from the system to frictionally disengage the stent from the remaining portions of the system. The remaining portions of the system are then withdrawn from the stent. Thus, the Kwart retro-inject system is not an end-to-end coupling mechanism, the elements are used in coaxial relation. Furthermore, because the various components must be specifically sized relative to one another in order to achieve the desired frictional relationship, the system lacks versatility with respect to stent diameters. For any given stent diameter, a separate placement system dedicated to that diameter is required.

It is desirable, therefore, that a guidewire instrument placement method and apparatus provide a broader range of positioning control capability across a broader range of instrument placement methods and devices. It is particularly desirable that better grasp and release features be available for instrument placement over an in-place guidewire.

SUMMARY OF THE INVENTION

In accordance with a preferred embodiment of the present invention, end-to-end coupling between a placement instrument and an instrument to be placed is provided in the context of guidewire assisted instrument placement. The distal end of the instrument to the place is slidably captured upon the guidewire and an elongate positioner engages in end-to-end relation the proximal end of the instrument to be placed. The practitioner enjoys improved control over the positioning of the instrument to be placed, and may attach several such systems slidably upon the guidewire. Once the instrument to be placed is suitably positioned, the end-to-end coupling arrangement allows quick and complete detachment between the instrument to be placed and the placement instrument. This insures that the instrument to be placed remains in its position without being dislodged by the removal of the positioning instrument.

According to one embodiment of the invention, the end-to-end coupling arrangement is formed by a loop resting within a slot and a stylet resting coaxially within the instrument whereby the stylet locks the loop within the slot formation. In a second embodiment of the present invention, a collapsible loop captures a tail formation of the other instrument in order to accomplish end-to-end coupling. In a third embodiment of the invention, a flared distal end of an inner sleeve captures a tail formation of the instrument to be placed between the inner sleeve and an outer sleeve to accomplish end-to-end coupling.

BRIEF DESCRIPTION OF THE DRAWINGS

The invention will be more particularly described with reference to preferred embodiments as illustrated in the accompanying drawings, in which.

DETAILED DESCRIPTION OF THE INVENTION

Instrument placement as applied to suprapubic instrument placement uses a placement device comprising a needle similar in shape to that of the urethral sound, slidably disposed within a sheath sized to suitably dilate the puncture made by the needle. The distal tip of the needle coupling means adjacent thereto configured such that it accepts and couples with a mating coupling means attached to the instrument, e.g., catheter to be pulled into the bladder. The preferred structure of the coupling means on the needle and the instrument to be pulled into the bladder is such that the instruments cannot be pulled apart in the direction of their longitudinal axis, yet may be disengaged in response to lateral forces. To more fully secure the needle and instrument while drawing the instrument into the bladder, the sheath is advanced over the tip of the needle to prevent the instrument coupling means from releasing from the needle tip coupling means.

Figures 1, 2:
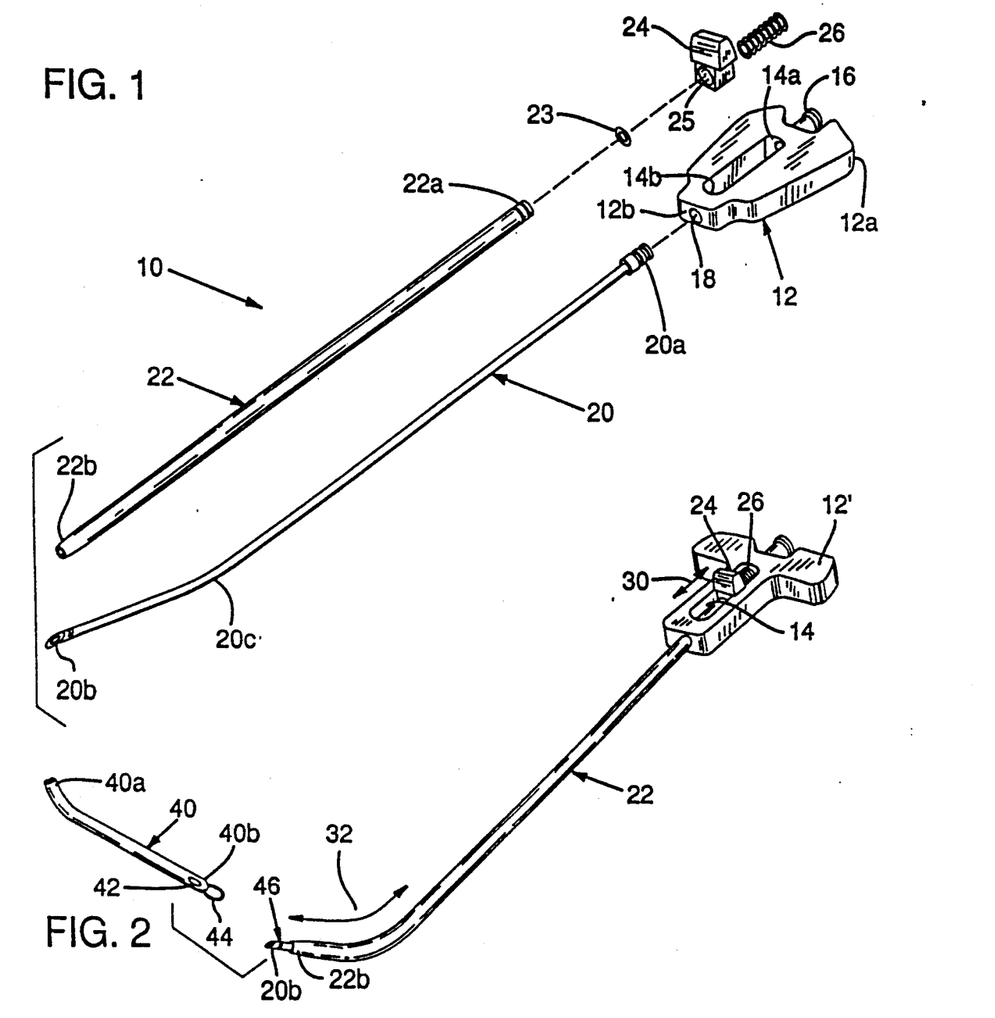
FIG. 1 is an exploded perspective view of a suprapubic instrument placement device in accordance with the present invention.
FIG. 2 illustrates a suprapubic instrument placement device similar to that of FIG. 1, but with an alternative handle shape and assembled to illustrate its coupling relationship to a catheter having a mating coupling means thereon.

In FIG. 1 of the drawings, a suprapubic instrument placement device 10 includes a handle 12 with a central slot 14 therein. A luer lock hub 16 is mounted upon handle 12 between the proximal end 12a of the handle and the proximal end 14a of the slot. At the distal end 14b of the slot, an aperture 18 coaxial to hub 16 passes from the distal end 12b of the handle to the distal end 14b of the slot. A rigid needle 20 is accommodated within aperture 18 and couples at its proximal end 20a to the hub 16 at the proximal end 14a of slot 14 In the illustrated embodiment needle 20 is substantially straight but includes a bend 20c to provide a distal end portion which makes an angle of approximately 15 degrees with the main portion of the needle whereby needle 20 conforms generally in shape to that of a urethral sound.

A flexible sheath 22 slidably mounts upon needle 20 and conforms to the shape of needle 20. A proximal end 22a of sheath 22 threadably connects to a thumb piece 24 at a threaded aperture 25 thereof. An O ring 23 is interposed between the proximal end 22a of sheath 22 and thumb piece 24 for sealably coupling sheath 22, thumb piece 24, and needle 20. Thumb piece 24 is slidably positionable within the slot 14 with a smaller diameter portion of aperture 25 (not shown) closely receiving needle 20 for slidable mounting thereon. The aperture 25 of thumb piece 24 is desirably of two diameters, a larger diameter threaded portion closest to distal slot end 14b adapted to receive the proximal end 22a of sheath 22 and the above-mentioned lesser diameter portion closest to proximal slot end 14a adapted for slidably receiving the needle 20. A spring 26 mounts coaxially upon the needle 20 near its proximal end 20a and is located between the thumb piece 24 and proximal slot end 14a to bias thumb piece 24 toward the distal slot end 14b.

The needle 20 is rigidly affixed to the handle 12 at hub 16. Thumb piece 24 is slidably positioned upon the portion of the needle 20 residing within slot 14. Also, spring 26 biases thumb piece 24 toward the distal end 14b of slot 14. The O ring 23 slides down the length of needle 20 and into slot 14 for positioning within the aperture 25 of thumb piece 24. Sheath 22 is then positioned upon needle 20 by inserting the distal end 20b of needle 20 through the proximal end 22a of sheath 22 whereby the proximal end 22a of sheath 22 may be threadably mounted within the aperture 25 of thumb piece 24. Accordingly, sheath 22 may be selectively mounted and dismounted from the device 10. It is contemplated that several such sheaths 22 may be provided of various diameters whereby a suitable sheath diameter may be selected corresponding to the diameter of the instrument to be suprapubicly placed. In this manner, sheath 22 performs a dilating function to closely match the diameter of the passageway provided between the bladder and the abdominal wall with the diameter of the instrument to be suprapubicly placed.

The proper relative length of needle 20 and sheath 22 as compared to the length of slot 14, i.e., range and movement for thumb piece 24, enables the user of device 10 to selectively expose the distal end 20b of needle 20 beyond the distal end 22b of sheath 22 by operation of thumb piece 24 within slot 14.

FIG. 2 illustrates a suprapubic instrument placement device 10 in its assembled configuration, but having a T shaped handle 12'. In other respects, the devices 10 of FIGS. 1 and 2 can be identical. The shape of handle 12 and handle 12' provides the practitioner with a reference for orientation of the distal end 20b of needle 20. A practitioner familiar with the shape and orientation of handle 12 relative to the orientation of needle 20 more accurately positions the distal end 20b of needle 20 during suprapubic instrument placement. In operation, needle 20 remains fixed relative to handle 12', but sheath 22 moves relative to handle 12' by movement of thumb piece 24 within slot 14. More particularly, movement of thumb piece 24 as indicated by arrows 30 corresponds to movement of the distal end 22b of sheath 22 relative to the distal end 20b of needle 20 as indicated by arrows 32. In this manner, the distal end 20b of needle 20 may be selectively exposed at the distal end 22b of sheath 22.

FIG. 2 also illustrates a catheter 40 including an inlet opening 42 for passage of fluids through catheter 40 to the proximal end 40a of catheter 40. The distal end 40b of catheter 40 includes a loop 44 comprising a length of filament material forming a closed loop and passing through a solid portion of the tip, i.e. the end 40b, of catheter 40. Loop 44 thereby provides a secure structure for attachment to an indentation or notch 46 adjacent to the distal end 20b of needle 20.

Figure 3:
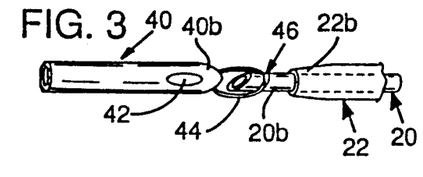
FIGS. 3 and 4 are detailed views of coupling means for releasably coupling and locking together the instrument placement device and the instrument to be drawn into the bladder.
Figure 4:
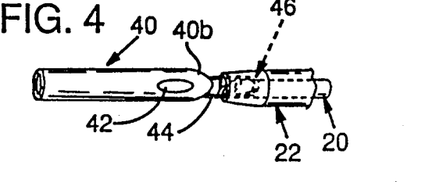

FIG. 3 is a detailed view of the end 40b of catheter 40 and distal end 20b of needle 20. FIG. 3 illustrates the coupling of the loop 44 and indentation 46. As shown in FIG. 3, the distal end 20b of needle 20 extends, by operation of thumb piece 24, beyond the distal end 22b of sheath 22 to expose the indentation 46. Indentation 46 receives the loop 44 of catheter 40 for coupling needle 20 and catheter 40. With reference to FIG. 4, once the loop 44 is positioned and retained within the indentation 46, the distal end 22b of sheath 22 may be advanced by movement of thumb piece 24 (FIG. 2), beyond the distal end 20b of needle 20. In such configuration, the loop 44 is drawn into sheath 22 and lockingly engaged with indentation 46.

Figures 5A, 5B, 5C, 5D, 5E, 5F:
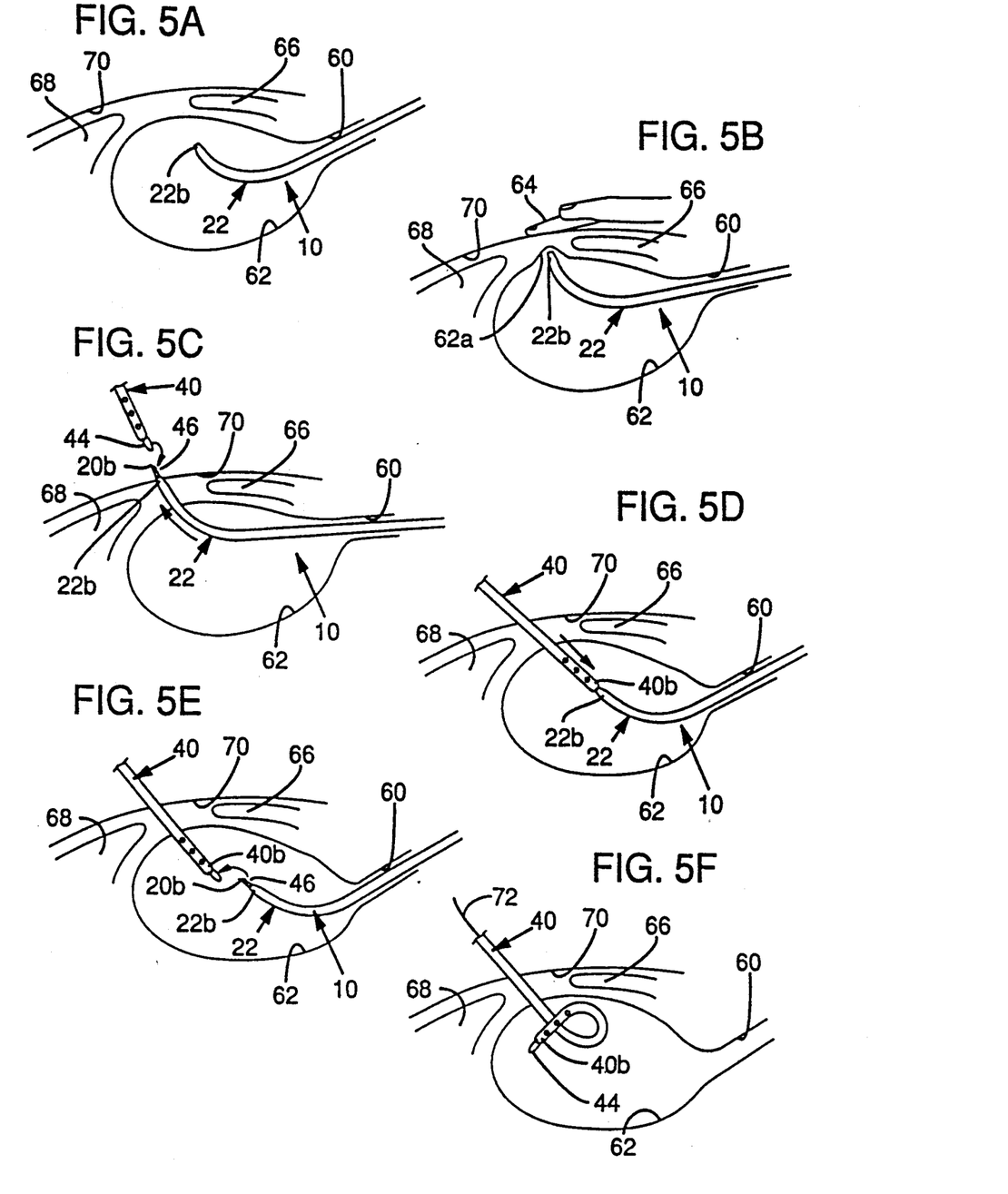
FIGS. 5A-5F illustrate suprapubic instrument placement according to the method of the present invention.

FIGS. 5A-5F illustrate suprapubic instrument placement by use of the device 10 and catheter 40. In FIG. 5A, the device 10 has been inserted through the urethra 60 to position the distal end 22b of sheath 22 within bladder 62. When placing device 10 within bladder 62 the thumb piece 24 is extended to the distal end 14b of slot 14 whereby sheath 22 shrouds the distal end 20b of needle 20. In FIG. 5B, device 10 is lifted against the dome 62a of bladder 62. The practitioner places his or her fingers 64 on the abdomen above the bladder to verify by palpation the positioning of the distal end 22b of device 10. More particularly, the practitioner must position the distal end 22b of device 10 just above the pubic bone 66 and just below the peritoneum 68.

Once the position of device 10 is verified as suitable for suprapubic instrument placement, the thumb piece 24 is drawn back to expose the distal end 20b of needle 20. The point of needle 20, i.e., the distal end 20b, may then be pushed, substantially longitudinally, through the fascia and abdominal wall 70 to the exterior of the abdominal wall 70 as shown in FIG. 5C. In certain cases, a small suprapubic incision may be made to assist advancement of the device 10 through the anterior abdominal wall 70. As shown in FIG. 5C, the distal end 20b of device 10 now protrudes out of the abdominal wall 70 exposing the indentation 46.

The loop 44 of catheter 40 is then coupled to the indentation 46 of device 10. Operation of thumb piece 24 then moves sheath 22 back over the distal end 20b of needle 20 to fully secure the catheter 40 and device 10. Referring now to FIG. 5D, the catheter 40 is then drawn through the abdominal wall 70 and into the bladder 62. Control of catheter location within the bladder is enhanced as traction can be applied at either end of the device assembly until the correct location is determined and the catheter released.

Turning to FIG. 5E, once the end 40b of catheter 40 is suitably positioned within bladder 62, thumb piece 24 is again actuated to expose the distal end 20b of needle 20. Lateral forces applied to the device 10 relative to the catheter 40 release the loop 44 of catheter 40 from the indentation 46. Device 10 may then be removed from the bladder 62 by way of the urethra 60. FIG. 5F shows final positioning of the catheter 40 within bladder 62. More particularly, in the illustrated example the catheter is a J-curve catheter which may be curled into the shape shown in FIG. 5F by withdrawing and securing a string 72 of catheter 40. Once so configured within the bladder 62, catheter 40 is operational.

Thus, the device and method of suprapubic instrument placement according to the present invention avoids many potential hazards of suprapubic instrument placement. For example, before penetrating the bladder wall or abdominal wall, the practitioner may accurately determine the location of the proposed site of catheterization by locating the instrument tip as illustrated in FIG. 5B. This insures that a proper instrument placement site is established.

The nature of the coupling mechanism between the instrument 10 and catheter 40 effects quick and convenient coupling and decoupling, yet provides a very secure coupling while drawing the catheter into the bladder. More particularly, the notch and loop configuration of the coupling means of device 10 and catheter 40 allow convenient coupling and decoupling of these devices, but because the sheath 22 may be positioned over the tip of needle 20, the loop 44 is securely held within the indentation 46. Once the catheter 40 is positioned within the bladder 62, exposing the needle tip and therefore the loop 44 and indentation 46 allows the practitioner to easily decouple the devices.

Additional features of the apparatus of the present invention offer the following benefits. Extravasation is minimized as the catheter size and sheath diameter may be closely matched, by selecting among a variety of sheaths 22, to improve the catheter-bladder seal. The control permitted by the apparatus facilitates its use under local anesthesia. Also, the apparatus may be adapted to place other instruments in the bladder such as cystotomy access tubes, cystourethroscopes, cystolithotriptors and instruments for the treatment of conditions of the bladder prostate urethra, and ureter.

Figures 6, 7:
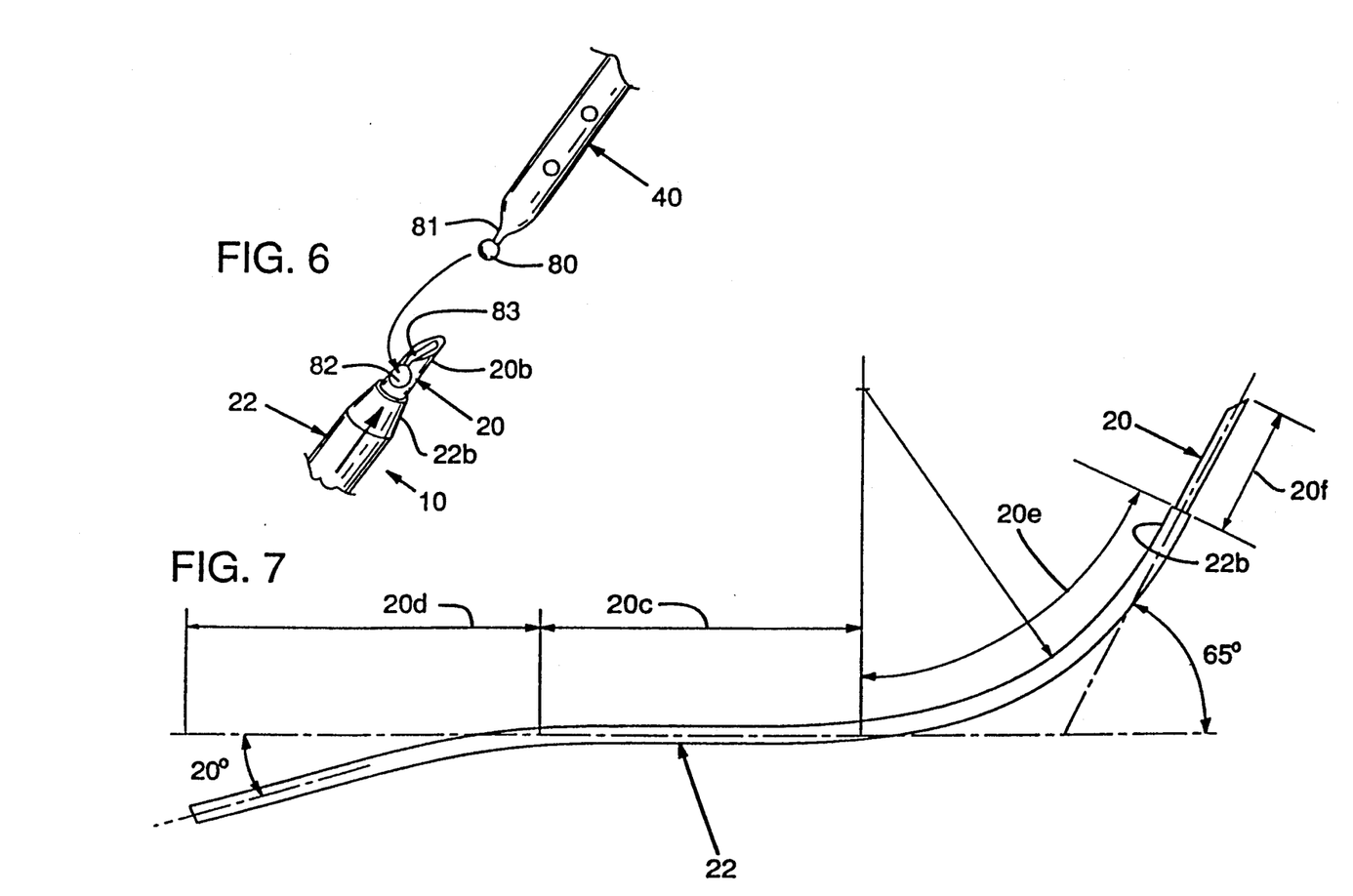
FIG. 6 illustrates an alternative coupling means in accordance with the present invention.
FIG. 7 is a needle and sheath arrangement adapted for placement within the male urethral sound.

FIG. 6 illustrates an alternative embodiment wherein the instrument coupling means comprises a ball 80 attached to the tip of a catheter 40 by a stem 81. A cavity 82 and groove 83 adjacent the distal end 20b of needle 20 receive the ball 80 and stem 81, respectively. To secure the catheter 40 of FIG. 6 and the device 10 of FIG. 6, the ball 80 is positioned within the cavity 82 and the stem within the groove 83. The sheath 22 may then be moved over the distal end 20b of needle 20 to fully secure the ball 80 within the cavity 82. The arrangement of FIG. 6 thereby provides convenient coupling and decoupling while providing a secure locking together of the device 10 and catheter 40 while drawing the catheter 40 into the bladder.

While a J-curve type catheter has been shown for use in connection with the device 10, many forms of catheter and other instruments, e.g. obturators, suitable for suprapubic instrument placement may be used in accordance with the present invention. For example, the types of suprapubic catheters applicable to the present invention include Foleys, Malecots, pigtails and loop-types. The ability to select and align the penetration site and pathway compared to actual penetration minimizes accidental perforation and catheter misplacement.

In the illustrated embodiments of FIGS. 1-5, the sheath-needle assembly comprises a 25 cm length, 13 gauge needle, which is shaped for a female urethra. FIG. 7 illustrates a configuration more suitable for the male urethra. In FIG. 7, needle 20 is shown extended approximately one inch beyond the distal end 22b of sheath 22. As previously described, the needle 20 is desirably a substantially rigid element while the sheath 22 is a flexible member adapted to conform in shape to that of needle 20 while being slidably disposed thereon. In this regard, rigidity in needle 20 may be achieved by use of a stepped-gauge or tapered-gauge needle. A central length portion 20c of needle 20 is approximately 2.5 inches, or 6.35 centimeters. The proximal length portion 20d of needle 20 is approximately three inches, or 7.62 centimeters, and aligned at approximately 20 degrees relative to length portion 20c. A distal length portion 20e of needle 20 is curved along a radius of approximately 2.625 inches, or 6.67 centimeters, extending from the central length portion 20c to the straight distal length portion 20f. The curvatures provided in the needle 20 maintain each length portion of needle 20 within a common plane, with the curvature of portion 20d relative to portion 20c being opposite that of the curvature of portion 20e relative to 20c, i.e., in opposite half-planes as defined by portion 20c. The configuration of needle 20 and sheath 22 as illustrated in FIG. 7 conforms to male anatomy while permitting proper angulation to select suprapubic placement and provide good transfer of longitudinal energy forces.

Suprapubic procedures, as made more available and practical by the present invention, offer many advantages. Suprapubic catheters provide increased patient comfort and minimization of infection in comparison to urethral catheters. Transurethral resection of prostate (TURP) irrigation via a suprapubic tube has been found to maximize visibility and speed resection time. Reduced morbidity and hospital stay can occur when percutaneous bladder procedures are used over open operations. Improving the ease and safety of suprapubic catheter and instrument placement encourages their broader use and allows their benefits to be more fully realized.

Inside-to-outside suprapubic instrument placement in accordance with the illustrated embodiments further provides full control over catheter placement; accurate suprapubic puncture location and orientation protection of penetrating element (needle); compatibility with a variety of catheter sizes and types; and coordination of puncture diameter with catheter size. Other benefits of suprapubic instrument placement as shown herein include the capability to fill or drain the bladder, via the needle. It is also possible to inject a local anesthetic through the needle, offering the potential for bedside placement of suprapubic catheters.

Limitations in the application of the apparatus and method of the present invention are few.

For example, in suprapubic instrument placement, urethral obstruction would not permit inside-to-outside access to the bladder. Obesity requires an assistant to pull up on the pannus and then depress down and toward the head. Control of catheter location is enhanced as traction can be applied at either end of the device assembly until the correct location is determined and the catheter is released. The apparatus in accordance with the present invention provides additional benefits such as minimization of extravasation since the catheter diameter and dilating sheath diameter can be closely matched to improve the catheter-bladder wall seal. Catheter loss during placement is substantially minimized the secure coupling between the placement device and the instrument to be placed. Thus, the illustrated devices offer practitioners, in various surgical fields, a less demanding, and more reliable option for the performance of suprapubic instrument placement.

In addition to the specific embodiments described and illustrated herein, other embodiments are contemplated within the scope of the invention. For example, a rigid sheath may be employed in combination with a flexible needle, or even two rigid components if applicable, wherein the shape of the sheath corresponds to a given anatomy. The coupling mechanism of the present invention is not limited to the inside-to-outside method as it is equally applicable to outside-to-inside methods. Also, the coupling means of the device may be located on the sheath as an alternative to a coupling means on the needle. Transfer tubes, catheters, stents, wire guides, scopes, and other instruments to permit diagnosis and operation may be modified for placement in accordance the present invention. Furthermore, by selecting a different placement site, a variety of instrument devices can be placed, e.g., for cardiovascular, gastroenterology laparoscopy and other situations where indirect means are employed.

Finally, the reliability and control of inside-to-outside suprapubic instrument placement as provided by the present invention will likely generate increased use of suprapubic devices and, therefore, further advance the art of urologic treatment.

Figure 8:
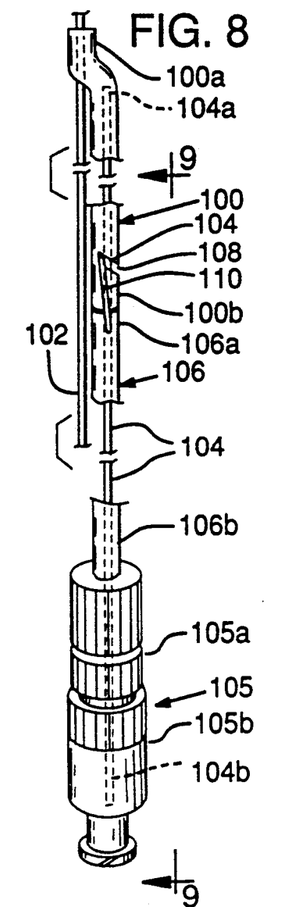
FIG. 8 illustrates an instrument placement system for use in conjunction with a guidewire.

FIG. 8 illustrates an instrument placement system for positioning a stent 100 in a body lumen, e.g., as an indwelling stent coupling a kidney and a bladder. The placement system of FIG. 8 includes a guidewire 102 which provides an access route along a selected body lumen. An internal stylet 104 rests coaxially within the stent 100 and engages at its distal end 104a the distal end 100a of stent 100 in pushing fashion. The stylet 104 frictionally engages the stent 100, or may engage a formation (not shown) of the stent 100, in order to provide a pushing force on the stent 100 and thereby drive the stent 100 along the guidewire 102. The stylet 104 also provides a stiffening function within the stent 100 to maintain the stent 100 in a substantially straight configuration.

The instrument placement system of FIG. 8 further includes a proximal positioner 106. The distal end 106a of the positioner 106 abuts in end-to-end relation the proximal end 100b of stent 100. The distal end 106a of positioner 106 includes a loop 110. The proximal end 100b of stent 100 carries slot 108. Loop 110 is of sufficient size to rest within the slot formation 108. The stent 100 is then locked end-to-end to the positioner 106 by positioning the loop 110 within slot 108 and sliding the stylet 104 coaxially through both the positioner 106 and the stent 100. The stylet 104 thereby captures the loop 110 within the slot 108 as illustrated in FIG. 8. The positioner 106 and stylet 104 are coupled at their proximal ends 106b and 104b by luer lock 105. More particularly, the proximal end 106b of positioner 106 terminates in and attaches to the portion 105a of lock 105. Stylet 104 rests coaxially within and slidably through portion 105a. The proximal end 104b of stylet 104 terminates in and attaches to the portion 105b of luer lock 105. The stylet 104 may be solid, or may include a central bore for passage of fluid therethrough in accordance with known practice.

Figure 9:
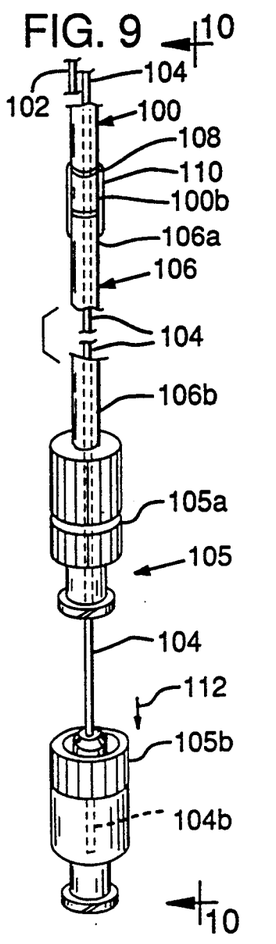
FIGS. 9 and 10 illustrate the uncoupling of the instrument placement system of FIG. 8.
Figure 10:
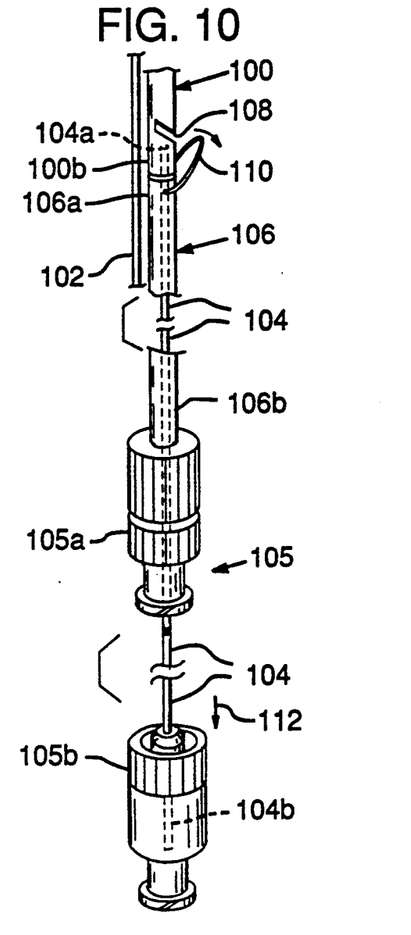

FIGS. 9 and 10 illustrate the unlocking of positioner 106 and stent 100 following placement of the stent 100.

In FIG. 9, the stylet 104 is retracted as indicated by the arrow 112 by decoupling and separating portions 105a and 105b of lock 105. In FIG. 10, the stylet 104 is retracted until a marker 114 emerges from the portion 105b of lock 105. The emergence of marker 114 corresponds to the passage of the distal end 104a of stylet 104 past the slot formation 108. Once the distal end 104a of stylet 104 passes the slot 108, the loop 110 is free to move out of the slot 108 as indicated by the arrow 116. The stent 100 may be preloaded to naturally assume a curled configuration upon the removal of the stylet 104. This natural curling of the stent 100 helps bring the loop 110 out of the slot 108 when the stylet 104 exits the stent 100. Also, it is suggested that the slot 108 be angled with respect to the longitudinal axis of stent 100 in such manner to better facilitate the removal of loop 110 therefrom, e.g., the deepest portion of slot 108 being most removed longitudinally from loop 110.

Figure 11A:
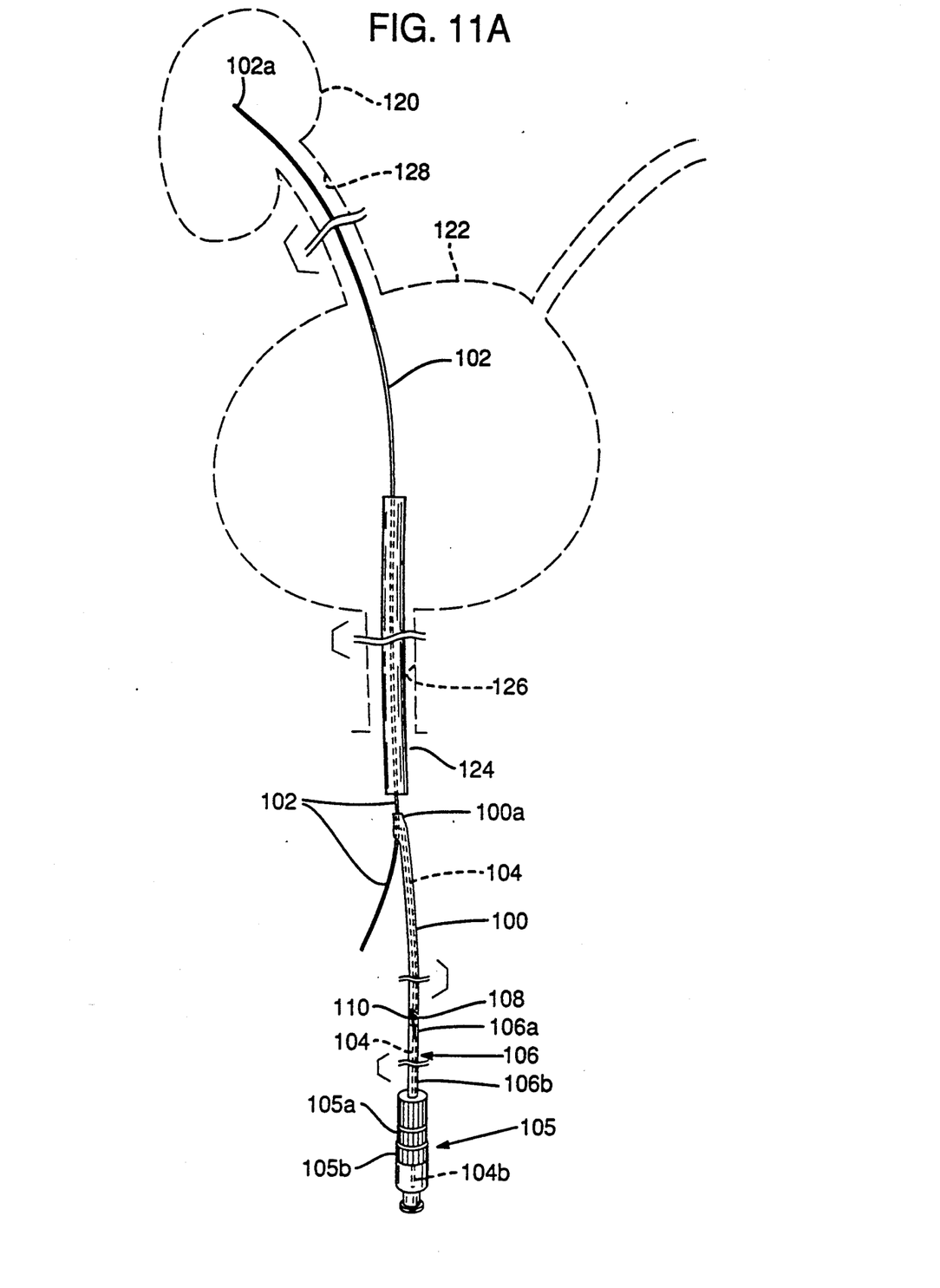
FIGS. 11A-11C illustrate in-dwelling stent placement for coupling a kidney and a bladder by use of a guidewire and cystoscope according to the embodiment of FIG. 8.

FIGS. 11A-11C illustrate in-dwelling placement of the stent 100 for coupling a kidney 120 and a bladder 122. In FIG. 11A, a cystoscope 124 has been positioned within the urethra 126 and terminates in the bladder 122. The guidewire 102 rests coaxially within the cystoscope 124 and extends from the distal end of the cystoscope 124 up through the ureter 128 and into the kidney 120. The distal end 100a of stent 100 is slidably mounted upon the guidewire 102. The stent 100 is coupled to the positioner 106 as shown in FIG. 8 and the stylet 104 rests coaxially within the positioner 106 and the stent 100 as shown in FIG. 8. The luer lock 105 is joined together to lock the stylet 104 and positioner 106 in fixed relative longitudinal position.

The placement system is then ready for sliding along the guidewire 102 through the cystoscope 124 and into the desired position. Movement of the system along the guidewire 102 is facilitated by the column strength provided by the stylet 104 and the coupling of stylet 104 and positioner 106 at the lock 105. As may be appreciated, and as discussed in U.S. Pat. No. 4,824,435, the disclosure of which is incorporated fully herein by reference, a separate pusher can be slidably mounted on the guidewire 102 and engage the distal end 100a of stent 100 in order to slide the stent 100 along the guidewire 102.

Figure 11B:
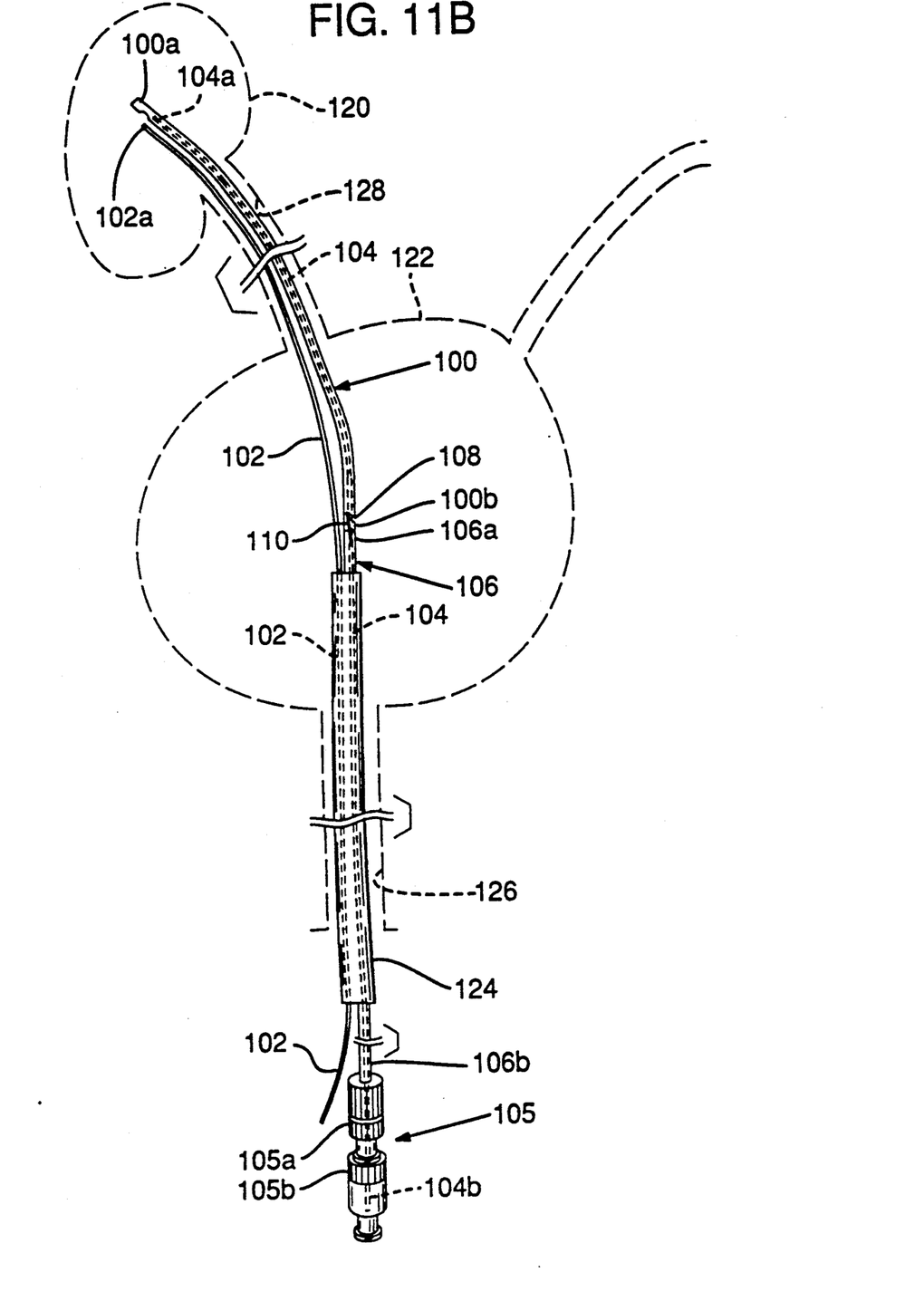
Figure 11C:
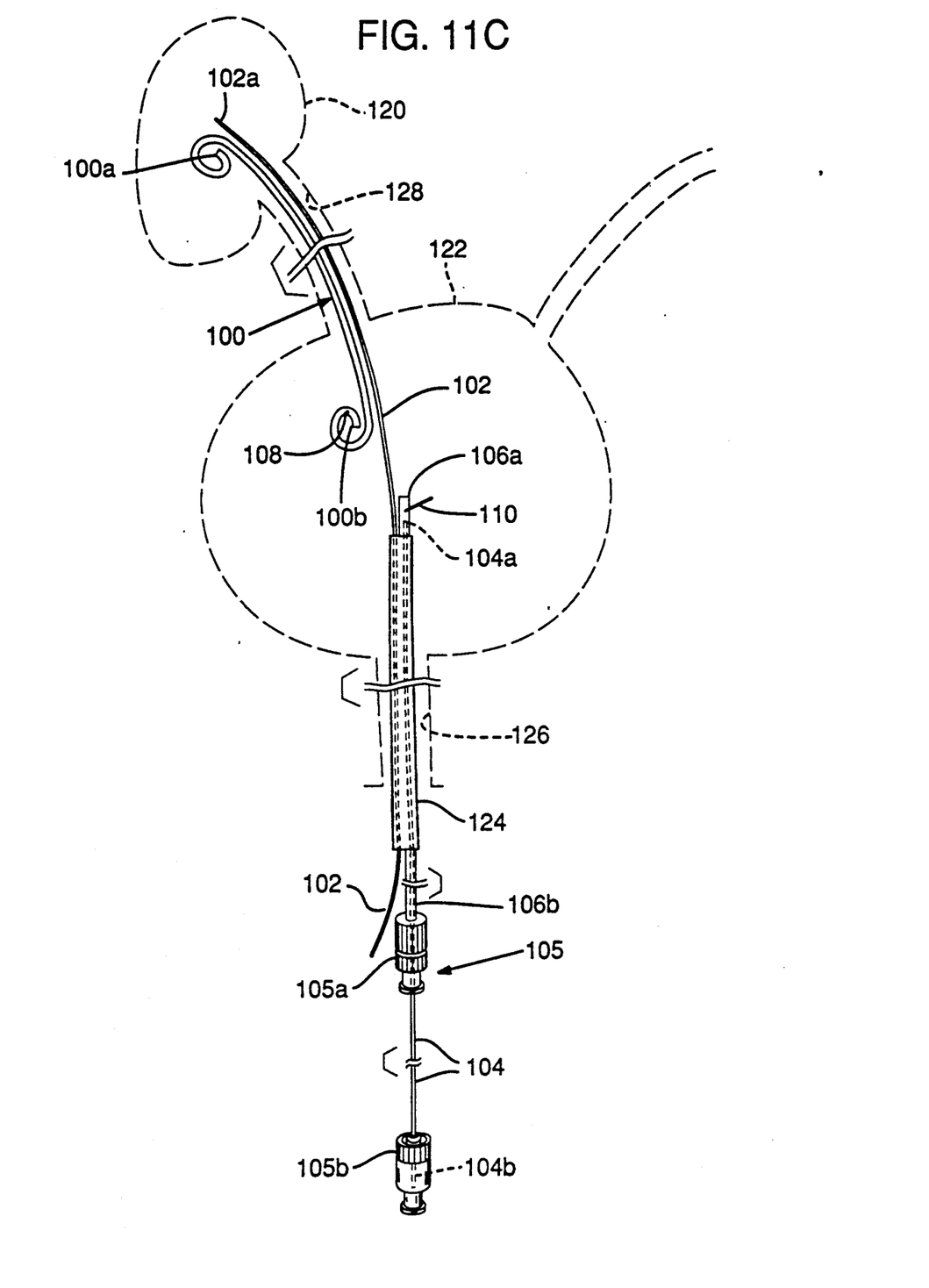

FIG. 11B shows the placement system after having pushed the stent 100 into position within ureter 128 to better fluidly couple the kidney 120 and bladder 122. The distal end 100a of stent 100 has been pushed off the distal end 102a of guidewire 102 thereby making the placement system free of the guidewire 102. Guidewire 102 can be removed at this time, or left in place for other uses. The stent 100 then has its distal end 100a within the kidney 120 and its proximal end 100b within the bladder 122. The system is now ready for uncoupling. Uncoupling is accomplished by retraction of the stylet 104 as indicated by arrow 112, i.e., uncoupling and separation of luer lock 105. As discussed above in connection with FIGS. 9 and 10, the stylet is retracted until the marker 114 (FIG. 10) emerges from the portion 105a of lock 105. This indicates that the distal end 104a of stylet 104 has passed the slot 108. Turning to FIG. 11C, the stylet has passed the slot 108, the loop 110 falls from slot 108, and stent 100 assumes its natural curled configuration. Stent 100 is thereby decoupled from the positioner 106 as shown in FIG. 11C. The stylet 104 is then completely removed from the positioner 106, and the positioner 106 can be removed from the cystoscope 124. The stent 100 is now in operational position coupling the kidney 120 and the bladder 122. The guidewire 102 and cystoscope 124 may then be used for other associated procedures, or may be removed if no longer needed.

Figure 12:
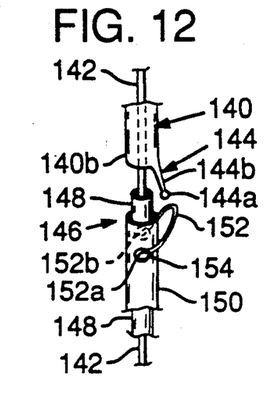
FIGS. 12-14 illustrate a second instrument placement system for use in conjunction with a guidewire.

FIGS. 12-15 illustrate a second instrument placement system for use in conjunction with a guidewire. In FIG. 12, a stent 140 rests coaxially upon a guidewire 142. The proximal end 140b of stent 140 carries a tail 144, in this particular embodiment a tail 144 defining a ball 144a and stem 144b. In other implementations of the present invention, the tail at the proximal end 140b of stent 140 may simply be an extension of the stent wall structure, or soft material well captured by a collapsible loop 152 of the positioner system 146. For example, the tail 172 illustrated in FIGS. 16 and 17 could be used in connection with the loop 152 of the embodiment of FIGS. 12-14. A positioner system 146 rests coaxially upon the guidewire 142. The positioner system 146 includes an inner sleeve 148 and an outer sleeve 150. The sleeves 148 and 150 are allowed relative longitudinal sliding movement. Loop 152 at the distal end of sleeve 148 is attached at one end 152a and at the other end 152b to the inner sleeve 148, extending through apertures 154 of outer sleeve 150. Thus, the loop 152 may be collapsed against the outer surface of sleeve 150 by relative movement between the sleeves 148 and 150.

Figure 13:
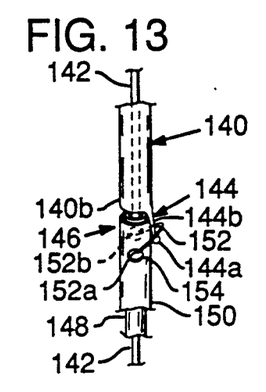
Figure 14:
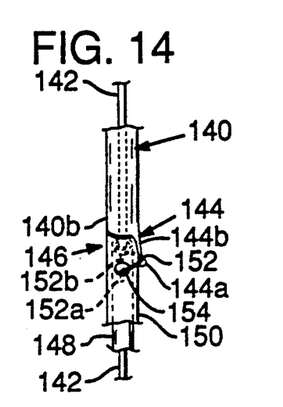

FIGS. 13 and 14 illustrate the locking procedure for coupling together in end-to-end relation the stent 140 and the positioner system 146. In FIG. 13, the sleeves 148 and 150 are positioned relative to one another such that the loop 152 is expanded. The inner sleeve 148 is brought into abutment with the proximal end 140b of stent 140 and the tail 144 is inserted through the loop 152. The system is now ready for locking together in end-to-end relation the stent 140 and the positioner system 146.

In FIG. 14, the inner sleeve 148 is retracted within outer sleeve 150 for relative longitudinal movement of the inner sleeve 148 as indicated by the arrow 158, i.e., retracting movement of sleeve 148 relative to sleeve 150. Such relative longitudinal movement of sleeves 148 and 150 collapses the loop 152 against the outside of sleeve 150 and thereby captures the tail 144 at the loop 152.

Figure 15A:
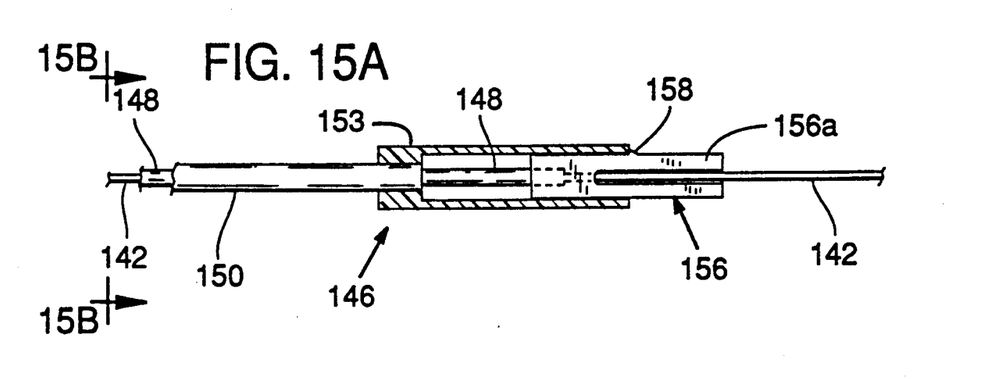
FIG. 15 illustrates a handle locking arrangement for the proximal end of the instrument placement system of FIGS. 12-14.
Figure 15B:
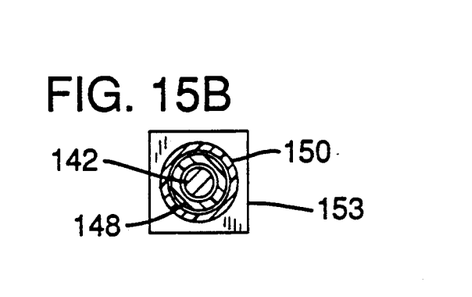

FIGS. 15A and 15B illustrate a locking arrangement for the positioning system 146. In FIGS. 15A and 15B, outer sleeve 150 attaches to a handle 152. Inner sleeve 148 extends slidably into a cavity 154 of handle 153 and attaches to a locking inner handle 156 slidably disposed within the cavity 154. Handle 156 includes a resilient portion 156a carrying a catch 158. Resilient portion 156a may be pressed downward to allow sliding of the locking inner handle 156 into the cavity 154 to thereby fully expand the loop 152. By retracting the handle 156 from the cavity 154, the catch 158 engages a rear edge of handle 153 and prevents handle 156 from re-entering cavity 154. By suitably dimensioning the handle 153, handle 156, and positioning of catch 158, the loop 152 may be suitably closed upon engagement of catch 158 at the rear edge of handle 153. Furthermore, the locking arrangement of FIG. 15 may accommodate a central bore for accommodating the guidewire 142 therethrough. As may be appreciated, the locking arrangement can be operated, i.e., locked, by manipulation at the distal ends of sleeves 148 and 150. The practitioner need not manipulate handles 153 and 156 when loading a stent.

The positioner system 146 is thereby positively locked to the stent 140 to provide pushing and pulling control over the stent 140 as well as twisting control over the stent 140. The extent of twisting control is determined by the specific configuration of the tail 144. In the particular embodiment illustrated, to the extent that the length of stem portion 144b can be minimized, the twisting control over stent 140 may be increased.

A typical problem encountered by the practitioner is limited guidewire length available at the proximal, exposed end of the guidewire. The instrument placement system illustrated in FIGS. 12–15 addresses this problem. In use of the instrument placement system of FIGS. 12–14, once the guidewire 142 is positioned, the stent 140 is positioned on the guidewire 142 by sliding the stent coaxially along the guidewire 142. This requires, at most, only enough exposed guidewire 142 length to cover slightly more than the length of stent 140. In other words, if the available guidewire length is slightly greater than the stent 140, then the length of stent 140 may be slidably and coaxially mounted upon the guidewire 140 while maintaining contact with the guidewire 140. In this manner, the guidewire 140 does not migrate in positioning of the stent 140 thereon.

Once the stent 140 is positioned along the guidewire 142, then the placement system 146 is slidably and coaxially mounted upon the guidewire 142 and locked to the stent 140 as discussed above. Once the system is so locked, the stent 140 may be positioned as desired. Once so positioned, the guidewire 142 is retracted from the instrument placement system. Once the wire 142 is removed, the stent 140 is decoupled from the placement system 146 by operation of handle 152 (FIG. 15).

Figure 16:
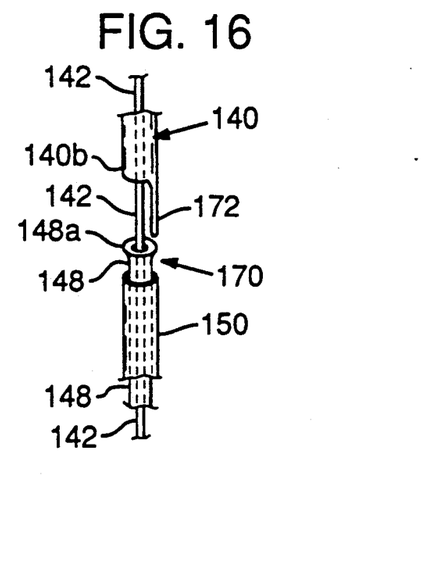
FIGS. 16 and 17 show an alternative locking arrangement for the distal end of the instrument placement system of FIGS. 12-14.
Figure 17:
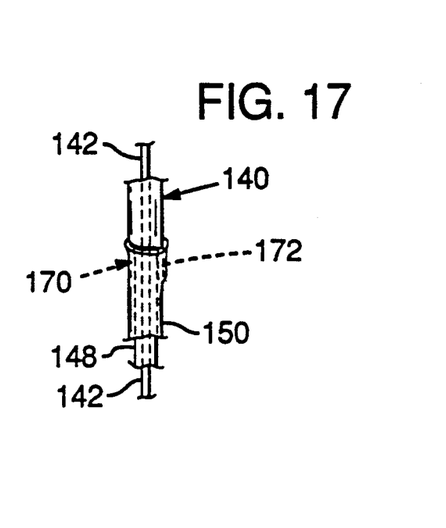

FIGS. 16 and 17 illustrate an alternative locking arrangement for the instrument placement system of FIGS. 12–15. In FIG. 16, the inner sleeve 148 includes at its distal end 148a a flared end configuration to provide an adjacent relatively smaller diameter recess 170. The stent 140 includes a tail 172 integrally formed as an extension of the wall structure of stent 140. The system generally operates in the same fashion as described above. The stent 140, inner sleeve 148 and outer sleeve 150 each rest coaxially relative to the guidewire 142 with the stent in end-to-end relation to the sleeves 148 and 150. Locking of the stent 140 to the sleeves 148 and 150 is accomplished by placing the stent 140 in end-to-end abutment relative to the proximal end 148a of sleeve 148 such that the tail 172 may rest within the recess formation 170. By then retracting the sleeve 148 within the sleeve 150, the tail 172 is captured within the recess formation 170 by the inner surface of the sleeve 150, as illustrated in FIG. 17.

Thus, an improved end-to-end coupling arrangement has been shown and described for use in connection with guidewire instrument placement. The end-to-end coupling arrangement provides a reliable coupling between a positioning system and an instrument to be positioned whereby pushing, pulling, and twisting capabilities are desired. While the illustrated system provides a positive lock between the instrument to be placed and the positioning system, such positive engagement can be easily and completely disengaged to establish a clean break between the instrument to be placed and the positioning system. Thus, the practitioner making use of the illustrated system can precisely achieve the desired instrument position, then completely disengage the positioning system and leave the positioned instrument undisturbed in the desired position. More particularly, in removing the positioning system from the body lumen the positioning system is completely decoupled and cannot affect the established instrument position. The illustrated system can be provided prepackaged with a guidewire, or may be used in connection with a separate guidewire previously positioned within a body lumen.

What is claimed is:

1. An instrument placement system for use in conjunction with a guide wire, the system comprising:
    an elongate instrument to be placed having a slide coupling for mounting slidably upon the guide wire;
    an elongate positioner; and
    an end-to-end coupling mechanism including a first coupling portion and a second coupling portion cooperative to join together in end-to-end relation said instrument to be placed and said positioner, said first coupling portion operative at a proximal end of said instrument to be placed and said second coupling portion operative at distal end of said positioner, said coupling mechanism further including a de-coupling portion operable exclusively at a proximal end of said positioner to release said first and second portions.

2. A system according to claim 1 wherein said first coupling portion is a tail attached to the instrument to be placed and the second coupling mechanism is attached to the positioner and adapted to selectively capture said tail.

3. A system according to claim 1 wherein one of said first and second coupling portions is a loop formation and the other one of said first and second coupling portions is stylet co-axially received within said instrument to be placed and co-axially received within said positioner and cooperative with a slot formation to capture said loop within said slot by blocking exit of said loop by said stylet.

4. A system according to claim 1 wherein one of said first and second coupling portions is a tail attached to the corresponding one of said instrument to be placed and said positioner and the other one of said first and second coupling portions comprises a loop collapsible to capture therein said tail.

5. A system according to claim 4 wherein said positioner defines said de-coupling portion as an inner sleeve and an outer sleeve in slidable concentric relative relation with said loop attach to one of said sleeves and restricted by at least one aperture of the other one of said sleeves such that relative longitudinal movement between said inner and outer sleeves accomplishes collapse and expansion of said loop.

6. A system according to claim 5 wherein said de-coupling portion further comprises:
    a lock handle including a first handle portion attached to said outer sleeve and a second handle portion attached to said inner sleeve and in sliding relation to said first handle portion; and
    a catch for maintaining a given position of said first handle portion relative to said second handle portion corresponding to a collapsed condition of said loop.

7. An instrument placement system for use in conjunction with a guide wire, the system comprising:
    an elongate instrument to be placed having a slide coupling for mounting slidably upon the guide wire;
    an elongate positioner; and an end-to-end coupling mechanism including a first coupling portion and a second coupling portion cooperative to join together in end-to-end relation said instrument to be placed and said positioner, said first coupling portion operative at a proximal end of said instrument to be placed and said second coupling portion operative at distal end of said positioner, said coupling mechanism further including a de-coupling portion operable at a proximal end of said positioner to release said first and second portions said first coupling portion being a tail attached to the instrument to be placed and said second coupling mechanism being attached to the positioner and adapted to selectively capture said tail, said positioner defining said de-coupling portion as an inner sleeve and an outer sleeve in slidable concentric relative relation, the distal end of said inner sleeve defining a flare formation and adjacent thereto a length portion of less diameter relative to said flare formation whereby said tail may be captured at said flare formation and between the inner and outer sleeves by relative longitudinal movement between said inner and outer sleeves.

8. A system according to claim 7 wherein said de-coupling portion further comprises:

a lock handle including a first handle portion attached to said outer sleeve and a second handle portion attached to said inner sleeve and in sliding relation to said first handle portion; and a catch for maintaining a given position of said first handle portion relative to said second handle portion corresponding said flare formation being substantially coincident with the distal end of said outer sleeve.

* * * * *